(12) United States Patent
Laibelman et al.

(10) Patent No.: US 6,667,306 B1
(45) Date of Patent: Dec. 23, 2003

(54) PLATELET ADP RECEPTOR INHIBITORS

(75) Inventors: Alan M. Laibelman, San Mateo, CA (US); Hans-Michael Jantzen, San Francisco, CA (US); Pamela B. Conley, Palo Alto, CA (US); Larry J. Fretto, Palo Alto, CA (US); Robert M. Scarborough, Belmont, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/226,103

(22) Filed: Jan. 7, 1999

Related U.S. Application Data

(60) Provisional application No. 60/092,109, filed on Jan. 15, 1998.

(51) Int. Cl.[7] ..................... C07D 513/14; A61K 31/549
(52) U.S. Cl. ......................... 514/222.8; 544/9; 544/6
(58) Field of Search ........................... 544/9, 6, 10, 11, 544/12, 13; 514/223.2, 222.8

(56) References Cited

U.S. PATENT DOCUMENTS

| | | | |
|---|---|---|---|
| 5,208,237 A | 5/1993 | Hewawasam et al. | 514/254 |
| 5,403,837 A | * 4/1995 | Audiau et al. | 514/222.8 |
| 5,681,823 A | 10/1997 | Kim et al. | 514/47 |

FOREIGN PATENT DOCUMENTS

| | | |
|---|---|---|
| WO | WO 89/04321 | 5/1989 |
| WO | WO 92/17488 | 10/1992 |

OTHER PUBLICATIONS

Allen, C.F.H. et al., *Organic Syntheses Collective*, 3, "2–Amino–6–Methylbenzothiazole", pp. 76–78 (1955).
Bundgaard, H., *Design of Prodrugs*, pp. 7–24 (1985).
Chan, S.W. et al., *Proceedings of the National Academy of Sciences of the United States of America*, "P, $P^4$–Dithio–$P^2$, $P^3$–Monochloromethylene Diadenosine 5',5"'–$P^1$, $P^4$–Tetraphosphate: A Novel Antiplatelet Agent" 94, No. 8, pp. 4034–4039 (1997).
Fratantoni, J.C., *American Journal of Clinical Pathology*, "Measuring Platelet Aggregation with Microplate Reader", 94, pp. 613–617 (1990).
Gachet, C. et al., *Thrombosis and Haemostasis*, "Activation of ADP Receptors and Platelet Function", 78, No. 1, pp. 271–275 (1997).
Grynkiewicz, G. et al., *The Journal of Biological Chemistry*, "A New Generation of $Ca^{2+}$ Indicators with Greatly Improved Fluorescence Properties", 260, No. 6, pp. 3440–3450 (1985).
Harden, T.K. et al., *Annual Review of Pharmacology and Toxicology*, "$P_2$–Purinergic Receptors: Subtype–Associated Signaling Responses and Structure", 35, pp. 541–579 (1995).
Hourani, S.M.O. et al., *Trends in Pharmacological Sciences Including Toxicological Sciences*, "Receptors for ADP on Human Blood Platelets", 15, pp. 103–108 (1994).
Humphries, R.G. et al., *Trends in Pharmacological Sciences Including Toxicological Sciences*, "A Novel Series of $P_{2T}$Purinoceptor Antagonists: Definition of the Role of ADP in Arterial Thrombosis", 16, pp. 179–181 (1995).
Kim, B.K. et al., *Proceedings of the National Academy of Sciences of the United States of America*, "Antithrombotic Effect of β, β'–monochloromethylene Diadenosine 5', 5"'–P, $P^4$–Tetraphosphate", 89, pp. 11056–11058 (1992).
Mangold, B.L.K et al., *Journal of Medicinal Chemistry*, "Arylhydroxamic Acid N,O–Acyltransferase Substrates. Acetyl Transfer and Electrophile Generating Activity of N–Hydroxy–N–(4–alkyl, 4–alkenyl–, and 4–cyclohexylphenyl)acetamides", 25, pp. 630–638 (1982).
Mills, D.C.B., *Thrombosis and Haemostasis*, "ADP Receptors on Platelets", 76, No. 6, pp. 823–856 (1996).
North, R.A. et al., *Current Opinion in Neurobiology*, "Nucleotide Receptors", 7, No. 3, pp. 346–357 (1997).
Sam, J. et al., *Journal of Pharmaceutical Sciences*, "Benzoxazoles: Potent Skeletal Muscle Relaxants", 53, pp. 538–544 (1964).
Savi, P. et al., *The Journal of Pharmacology and Experimental Therapeutics*, "Binding of [3H]–2–Methylthio ADP to Rat Platelets—Effect of Clopidogrel and Ticlopidine", 269, No. 2, pp. 772–777 (1994).
Savi, P. et al., *Medicinal Research Reviews*, "ADP Receptors on Platelets and ADP–Selective Antiaggregating Agents", 16, No. 2, pp. 159–179 (1996).
Schachter, J.B., *Birtish Journal of Pharmacology*, "Second Messenger Cascade Specificity and Pharmacological Selectivity of the Human $P_{2Y1}$–Purinoceptor", 118, pp. 167–173 (1996).
Silverman, R.B., *The Organic Chemistry of Drug Design and Drug Action*, "Prodrugs and Drug Delivery Systems", pp. 352–401 (1992).

* cited by examiner

*Primary Examiner*—John M. Ford
(74) *Attorney, Agent, or Firm*—Townsend and Townsend and Crew LLP

(57) ABSTRACT

The invention relates to novel compounds of formula (I) containing fused heterocyclic ring systems which are effective platelet ADP receptor inhibitors:

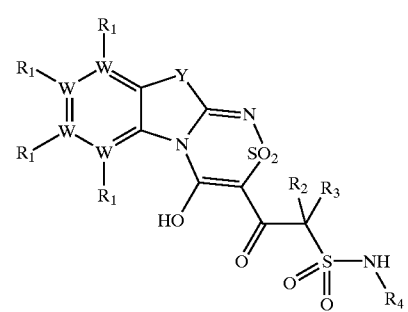

In formula (I), W is carbon or nitrogen, wherein at least one W is a carbon; and Y is nitrogen, oxygen, or sulfur. Such compounds including pharmaceutically acceptable salts are useful in various pharmaceutical compositions for the prevention and/or treatment of cardiovascular disease particularly those related to thrombosis.

15 Claims, No Drawings

PLATELET ADP RECEPTOR INHIBITORS

This application claims the benefit of Provisional Application Ser. No. 60/092,109 filed Jan. 15, 1998.

FIELD OF THE INVENTION

The invention relates to novel heterocycles containing aminobenzothiazole and aminobenzoxazole derivatives which are effective platelet ADP receptor inhibitors. These derivatives may be used in various pharmaceutical compositions. In particular, the derivatives may be used in pharmaceutical compositions effective for the prevention and/or treatment of cardiovascular diseases, particularly those diseases related to thrombosis.

DESCRIPTION OF THE RELATED ART

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and protheses. It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules such as collagen, or by thrombin which is formed in the coagulation cascade.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. ADP activates platelets through specific platelet ADP receptors, sometimes referred to as $P_{2T}$ receptors (Hourani et al., *Trends Pharmacol. Sci.* 15, 103 (1994); Savi et al., *Med Res. Rev.* 16, 159 (1996); Mills, *Thromb. Hemost.* 76, 835 (1996); Gachet et al., *Thromb. Hemost.* 78, 271 (1997)). This results in the recruitment of more platelets and stabilization of existing platelet aggregates. Platelet ADP receptors mediating aggregation are activated by ADP and some of its derivatives and antagonized by ATP (adenosine 5'-triphosphate) and some of its derivatives. Therefore, platelet ADP receptors are members of the family of P2 receptors activated by purine and/or pyrimidine nucleotides (Harden et al., *Annu. Rev. Pharmacol. Toxicol.* 35, 541 (1995); North et al., *Curr. Opin. Neurobiol.* 7, 346 (1997)). Studies of inherited disorders in humans and rats which result in a reduction of ADP release from platelets or reduced ADP receptor number and signaling confirm the critical role in platelet aggregation of ADP and the ADP receptor itself. Potent inhibitors of ADP-induced platelet aggregation therefore might be useful as antithrombotic drugs.

Various directly or indirectly acting synthetic inhibitors of ADP-dependent platelet aggregation with antithrombotic activity have been reported. The orally active antithrombotic thienopyridines ticlopidine and clopidogrel inhibit ADP-induced platelet aggregation, binding of radiolabeled ADP receptor agonist 2-methylthioadenosine 5'-diphosphate to platelets, and other ADP-dependent events indirectly, probably via formation of an unknown metabolite, in humans or animals (Savi et al., *Med. Res. Rev.* 16, 159 (1996)). Some derivatives of the endogenous antagonist ATP, e.g., ARL (formerly FPL) 67085, are selective platelet ADP receptor antagonists which inhibit ADP-dependent platelet aggregation and are effective in animal thrombosis models (Mills, *Thromb. Hemost.* 76, 835 (1996); Humphries et al., *Trends Pharmacol. Sci.* 16, 179 (1995); WO 92/17488)). Derivatives of $P^1,P^4$-diadenosine 5', 5'''-$P^1,P^4$-tetraphosphate have also been reported to both inhibit ADP-dependent platelet aggregation in vitro and thrombosis in animal models (Kim et al., *Proc. Natl. Acad. Sci. USA* 89, 11056 (1992); Chan et al., *Proc. Natl. Acad Sci. USA* 94, 4034 (1997); U.S. Pat. No. 5,681,823; WO 89/04321).

Despite these compounds, there exists a need for more effective platelet ADP receptor inhibitors. In particular, there is a need for platelet ADP receptor inhibitors having anti-thrombotic activity that are useful in the prevention and/or treatment of cardiovascular diseases, particularly those related to thrombosis.

SUMMARY OF THE INVENTION

The invention provides compounds of formula (I):

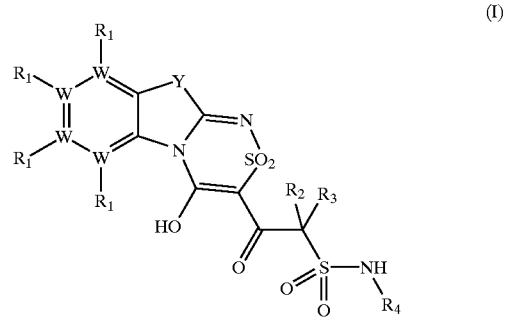

In another aspect, the invention provides pharmaceutical compositions for preventing or treating thrombosis in a mammal containing a therapeutically effective amount of a compound of formula (I) or a pharmaceutically acceptable salt thereof and a pharmaceutically acceptable carrier. The invention further provides a method for preventing or treating thrombosis in a mammal by administering a therapeutically effective amount of a compound of formula (I) or a pharmaceutically acceptable salt thereof.

DETAILED DESCRIPTION OF THE INVENTION

1. Definitions

In accordance with the invention and as used herein, the following terms are defined with the following meanings, unless explicitly stated otherwise.

The term "$C_1$–$C_6$ alkyl" as used herein refers to a straight or branched hydrocarbon containing one to six carbon atoms.

The term "$C_3$–$C_8$ cycloalkyl" as used herein refers to a cyclic aliphatic hydrocarbon containing three to eight carbon atoms.

The term "phenyl" as used herein refers to a six carbon containing aromatic ring which can be variously mono- or poly-substituted with H, $C_1$–$C_6$ alkyl, hydroxyl, $C_1$–$C_6$ alkoxy, amino, mono-$C_1$–$C_6$ alkylamino, di-$C_1$–$C_6$ alkylamino, nitro, fluoro, chloro, bromo, iodo, hydroxycarbonyl, or $C_1$–$C_6$ alkoxycarbonyl.

The term "$C_1$–$C_6$ alkoxy" as used herein refers to an ether moiety whereby the oxygen is connected to a straight or branched chain of carbon atoms of the number indicated.

The term "phenoxy" as used herein refers to an ether moiety whereby the oxygen is connected to a phenyl substituent, the latter being defined as above.

The term "mono-$C_1$–$C_6$ alkylamino" as used herein refers to an amino moiety whereby the nitrogen is substituted with one H and one $C_1$–$C_6$ alkyl substituent, the latter being defined as above.

The term "di-$C_1$–$C_6$ alkylamino" as used herein refers to an amino moiety whereby the nitrogen is substituted with two $C_1$–$C_6$ alkyl substituents as defined above.

The term "monoarylamino" as used herein refers to an amino moiety whereby the nitrogen is substituted with one H and one aryl substituent, such as a phenyl, the latter being defined as above.

The term "diarylamino" as used herein refers to an amino moiety whereby the nitrogen is substituted with two aryl substituents, such as phenyl, the latter being defined as above.

The term "$C_1$–$C_6$ alkylsulfonyl" as used herein refers to a dioxosulfur moiety with the sulfur atom also connected to one $C_1$–$C_6$ alkyl substituent, the latter being defined as above.

The term "$C_1$–$C_6$ alkoxycarbonyl" as used herein refers to a hydroxycarbonyl moiety whereby the hydrogen is replaced by a $C_1$–$C_6$ alkyl substituent, the latter being defined as above.

The term "heterocyclic group" as used herein refers to any saturated or unsaturated mono- or bicyclic ring system, containing from one to five heteroatoms. Each heteroatom may independently be nitrogen, oxygen or sulfur. Examples of suitable heterocyclic groups include, but are not limited to, piperidyl, pyrrolidinyl, pyridyl, piperazinyl, piperidonyl, thiazolyl, benzimidazolyl, benzothiazolyl, benzoxazolyl, pyridoxazolyl, pyridothiazolyl, pyridazinoxazolyl, pyridazinothiazolyl, pyrimidothiazolyl, pyrimidoxazolyl, pyrazinothiazolyl, pyrazinoxazolyl, triazinothiazolyl, and triazinoxazolyl.

A "pharmaceutically acceptable acid addition salt" refers to those salts which retain the biological effectiveness and properties of the free bases and which are not biologically or otherwise undesirable. The salts may be formed with inorganic acids such as, but not limited to, hydrochloric acid, hydrobromic acid, sulfuric acid, nitric acid, phosphoric acid and the like, or organic acids such as, but not limited to, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic. acid, salicylic acid and the like.

Similarly, "pharmaceutically acceptable base addition salts" include but are not limited to those derived from inorganic bases such as sodium, potassium, lithium, ammonium, calcium, magnesium, iron, zinc, copper, manganese, and aluminum bases, and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, dicyclohexylamine, lysine, arginine, histidine, caffeine, procaine, choline, betaine, ethylenediamine, glucosamine, methylglucamine, theobromine, purines, piperazine, piperidine, N-ethylpiperidine, polyamine resins and the like. Particularly preferred organic nontoxic bases are isopropyl amine, diethylamine, ethanolamine, trimethylamine, dicyclohexylamine, choline and caffeine.

"Biological property" for the purposes herein means an in vitro or in vivo biological effect or an antigenic function or activity that is directly or indirectly performed by a compound of the invention. Effect or functions include receptor or ligand binding, any enzyme activity or enzyme modulatory activity, any carrier binding activity, any hormonal activity, any activity in promoting or inhibiting adhesion of cells to an extracellular matrix or cell surface molecules, including the aggregation of platelets or any structural role. Antigenic functions include possession of an epitope or antigenic site that is capable of reacting with antibodies raised against it.

2. Compounds of the Invention

Compounds of formula (I) below represent one embodiment of the invention:

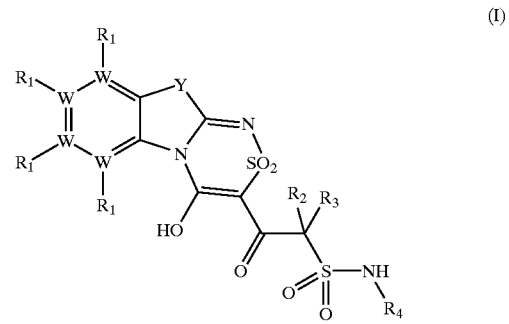

(I)

In formula (I):
W is carbon or nitrogen, wherein at least one W is a carbon;
Y is nitrogen, oxygen, or sulfur;
$R_1$ is, independently, H, $C_1$–$C_6$ alkyl, $C_3$–$C_8$ cycloalkyl, phenyl, pyridyl, pyrimidinyl, hydroxyl, $C_1C_6$ alkoxy, phenoxy, amino, mono-$C_1$–$C_6$ alkylamino, di-$C_1$–$C_6$ alkylamino, monoarylamino, diarylamino, nitro, fluoro, chloro, bromo, iodo, $C_1$–$C_6$ alkylsulfonyl, hydroxycarbonyl, $C_1$–$C_6$ alkoxycarbonyl, absent if W is a nitrogen, or adjacent $R_1$ groups together may form a five- or six-membered alicyclic ring, a six-membered aromatic ring, or a six-membered heteroaromatic ring containing one or two nitrogens, with the proviso that when a sequence of three W—$R_1$ groups form a N($R_1$)—C($R_1$)—N($R_1$) sequence, the $R_1$ bound to carbon is not a halogen;
$R_2$ and $R_3$ are, independently, H, $C_1$–$C_6$ alkyl, $C_3$–$C_8$ cycloalkyl, or $R_2$ and $R_3$ together form an alicyclic ring containing 3 to 8 carbon atoms; and
$R_4$ is a substituted or unsubstituted heterocyclic group containing at least one heteroatom of nitrogen, oxygen, or sulfur. Suitable substituents of $R_4$ include those groups encompassed by $R_1$.

In a preferred embodiment of a compound of formula (I):
W is carbon or nitrogen, wherein at least one W is a carbon;
Y is oxygen or sulfur;
$R_1$ is, independently, H, $C_1$–$C_6$ alkyl, phenyl, pyridyl, pyrimidinyl, $C_1$–$C_6$ alkoxy, phenoxy, amino, mono- $C_1$–$C_6$ alkylamino, di-$C_1$–$C_6$ alkylamino, $C_1$–$C_6$ alkylsulfonyl, absent if W is a nitrogen, or adjacent $R_1$ groups together form a six-membered aromatic ring, or a six-membered heteroaromatic ring containing one or two nitrogens, with the proviso that when a sequence of three W—$R_1$ groups form a N($R_1$)—C($R_1$)—N($R_1$) sequence, the $R_1$ bound to carbon is not a halogen;

$R_2$ and $R_3$ are, independently, H or $C_1$–$C_6$ alkyl; and $R_4$ is a substituted or unsubstituted heterocyclic group containing at least one heteroatom of nitrogen, oxygen, or sulfur. Suitable substituents of $R_4$ include those groups encompassed by $R_1$ as described herein.

In a more preferred embodiment of a compound of formula (I):

W is carbon;

Y is sulfur;

$R_1$ is, independently, H, pyridyl, pyrimidinyl, amino, mono-$C_1$–$C_6$ alkylamino, or di-$C_1$–$C_6$ alkylamino, with the proviso that $R_1$ at the 8-position is $C_1$–$C_6$ alkyl, pyridyl, pyrimidinyl, hydroxyl, $C_1$–$C_6$ alkoxy, amino, mono-$C_1$–$C_6$ alkylamino, di-$C_1$–$C_6$ alkylamino, or $C_1$–$C_6$ alkylsulfonyl;

$R_2$ and $R_3$ are each a hydrogen; and $R_4$ is a substituted or unsubstituted heterocyclic group containing at least one heteroatom of nitrogen, oxygen, or sulfur. Suitable substituents of $R_4$ include those groups encompassed by $R_1$ as described herein.

Examples of suitable substituted or unsubstituted $R_4$ groups of a compound of formula (I) include, but are not limited to, piperidyl, pyrrolidinyl, pyridyl, piperazinyl, piperidonyl, thiazolyl, benzimidazolyl, benzothiazolyl, benzoxazolyl, pyridoxazolyl, pyridothiazolyl, pyridazinoxazolyl, pyridazinothiazolyl, pyrimidothiazolyl, pyrimidoxazolyl, pyrazinothiazolyl, pyrazinoxazolyl, triazinothiazolyl, and triazinoxazolyl. Preferred $R_4$ groups include, but are not limited to, benzothiazolyl, benzoxazolyl, pyrido[2,3-d][1,3]oxazolyl, pyrido[2,3-d][1,3]thiazolyl, pyrido[3,4-d][1,3]oxazolyl, pyrido[3,4-d][1,3]thiazolyl, pyrido[4,3-d][1,3]oxazolyl, pyrido[4,3-d][1,3]thiazolyl, pyrido[3,2-d][1,3]oxazolyl, pyrido[3,2-d][1,3]thiazolyl, pyridazino[3,4-d][1,3]oxazolyl, pyridazino[3,4-d][1,3]thiazolyl, pyridazino[4,5-d][1,3]oxazolyl, pyridazino[4,5-d][1,3]thiazolyl, pyridazino[4,3-d][1,3]oxazolyl, pyridazino[4,3-d][1,3]thiazolyl, pyrimido[5,6-d][1,3]thiazolyl, pyrimido[5,6-d][1,3]oxazolyl, pyrimido[5,4-d][1,3]thiazolyl, pyrimido[5,4-d][1,3]oxazolyl, pyrazino[2,3-d][1,3]thiazolyl, pyrazino[2,3-d][1,3]oxazolyl, [1,2,3]triazino[4,5-d][1,3]thiazolyl, [1,2,3]triazino[4,5-d][1,3]oxazolyl, [1,2,4]triazino[6,5-d][1,3]thiazolyl, [1,2,4]triazino[6,5-d][1,3]oxazolyl, [1,2,4]triazino[5,6-d][1,3]thiazolyl, [1,2,4]triazino[5,6-d][1,3]oxazolyl, [1,2,3]triazino[5,4-d][1,3]thiazolyl, and [1,2,3]triazino[5,4-d][1,3]oxazolyl. These compounds are summarized in Table 1 below:

TABLE 1

$R_4$ groups of Compounds of Formula (I)

| $R_4$ group | Structure |
|---|---|
| benzothiazolyl | *(benzothiazole with R)* |
| benzoxazolyl | *(benzoxazole with R)* |
| pyrido[2,3-d][1,3]oxazolyl | *(fused pyridine-oxazole with R)* |
| pyrido[2,3-d][1,3]thiazolyl | *(fused pyridine-thiazole with R)* |
| pyrido[3,4-d][1,3]oxazolyl | *(fused pyridine-oxazole with R)* |
| pyrido[3,4-d][1,3]thiazolyl | *(fused pyridine-thiazole with R)* |
| pyrido[4,3-d][1,3]oxazolyl | *(fused pyridine-oxazole with R)* |
| pyrido[4,3-d][1,3]thiazolyl | *(fused pyridine-thiazole with R)* |
| pyrido[3,2-d][1,3]oxazolyl | *(fused pyridine-oxazole with R)* |
| pyrido[3,2-d][1,3]thiazolyl | *(fused pyridine-thiazole with R)* |
| pyridazino[3,4-d][1,3]oxazolyl | *(fused pyridazine-oxazole with R)* |
| pyridazino[3,4-d][1,3]thiazolyl | *(fused pyridazine-thiazole with R)* |
| pyridazino[4,5-d][1,3]oxazolyl | *(fused pyridazine-oxazole with R)* |
| pyridazino[4,5-d][1,3]thiazolyl | *(fused pyridazine-thiazole with R)* |

TABLE 1-continued

R₄ groups of Compounds of Formula (I)

| | |
|---|---|
| pyridazino[4,3-d][1,3]oxazolyl | |
| pyridazino[4,3-d][1,3]thiazolyl | |
| pyrimido[5,6-d][1,3]thiazolyl | |
| pyrimido[5,6-d][1,3]oxazolyl | |
| pyrimido[5,4-d][1,3]thiazolyl | |
| pyrimido[5,4-d][1,3]oxazolyl | |
| pyrazino[2,3-d][1,3]thiazolyl | |
| pyrazino[2,3-d][1,3]oxazolyl | |
| [1,2,3]triazino[4,5-d][1,3]thiazolyl | |
| [1,2,3]triazino[4,5-d][1,3]oxazolyl | |
| [1,2,4]triazino[6,5-d][1,3]thiazolyl | |
| [1,2,4]triazino[6,5-d][1,3]oxazolyl | |
| [1,2,4]triazino[5,6-d][1,3]thiazolyl | |

TABLE 1-continued

R₄ groups of Compounds of Formula (I)

| | |
|---|---|
| [1,2,4]triazino[5,6-d][1,3]oxazolyl | |
| [1,2,3]triazino[5,4-d][1,3]thiazolyl | |
| [1,2,3]triazino[5,4-d][1,3]oxazolyl | |

Another preferred embodiment of the compound of formula (I) is a compound of formula (II):

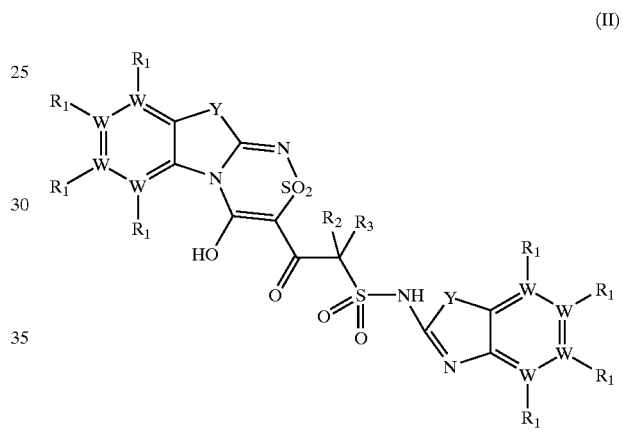

(II)

In formula (II), W, Y, $R_1$, $R_2$, and $R_3$ are each as defined above.

3. Preparation of Compounds of the Invention

A compounds of formula (I) may be prepared by reacting an aminoazole and chlorosulfonylacetyl chloride in an organic solvent in the presence of a molar excess of a tertiary amine base. Preferably, the molar ratio of aminoazole to chlorosulfonylacetyl ranges from about a 1:1, as shown by Scheme A, to about a 2:1, as shown by Scheme B.

Scheme A:

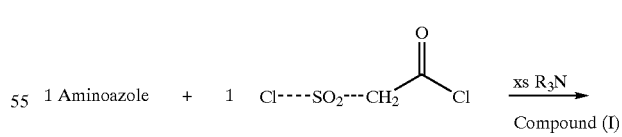

Scheme B:

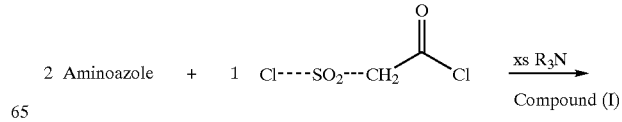

The aminoazole may be any commercially available aminoazole, including for example, substituted 2-aminobenzothiazole or 2-aminobenzoxazole derivatives. The aminoazole may also be prepared synthetically using techniques known in the art. For example, substituted 2-aminobenzoxazoles may be prepared according to the method outlined in Scheme I, where a substituted o-aminophenol is reacted with cyanogen bromide (Sam et al., *Journal of Pharmaceutical Sciences* 53, 538 (1964)):

SCHEME I

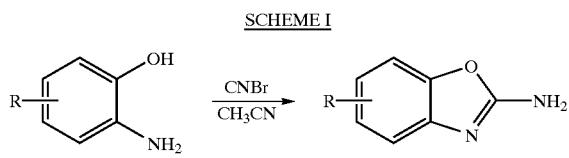

Similarly, substituted 2-aminobenzothiazoles may be prepared according to the method outlined in Scheme II, where a substituted aniline is reacted with ammonium thiocyanate in the presence of bromine or iodine (Mangold et al., *Journal of Medicinal Chemistry* 25, 630 (1982); Allen et al., *Organic Synthesis Collective* 3, 76 (1955)):

SCHEME II

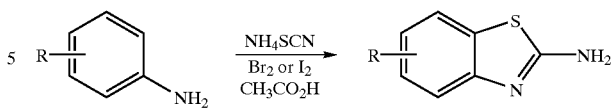

These procedures may also be followed to prepare pyrido-fused and pyrimido-fused aminoazoles by, for example, starting with commercially available materials such as 2-amino-3-hydroxypyridine or 4-aminopyrimidine.

Once prepared, pure aminoazoles may be isolated using typical isolation and purification techniques known in the art, such as solvent-solvent extraction and normal phase chromatography on silica gel. The pure aminoazole compounds may then be reacted in the usual manner as described above with chlorosulfonylacetyl chloride in the presence of a tertiary amine base to produce a compound of formula (I). Any tertiary amine base capable of acting as a neutralizing agent for the HCl generated upon reaction of the aminoazole with chlorosulfonylacetyl chloride may be used. Preferably the tertiary amine base is triethylamine or diisopropylethylamine. Likewise the organic solvent may be any solvent common to the practice of organic chemistry such as, for example, tetrahydrofuran, dichloromethane, chloroform, acetonitrile, and N,N-dimethylformamide. Preferably, the organic solvent is tetrahydrofuran.

Preferred methods for preparing compounds of formula (I) and of formula (II) are outlined in, respectively, Schemes III and IV:

SCHEME III

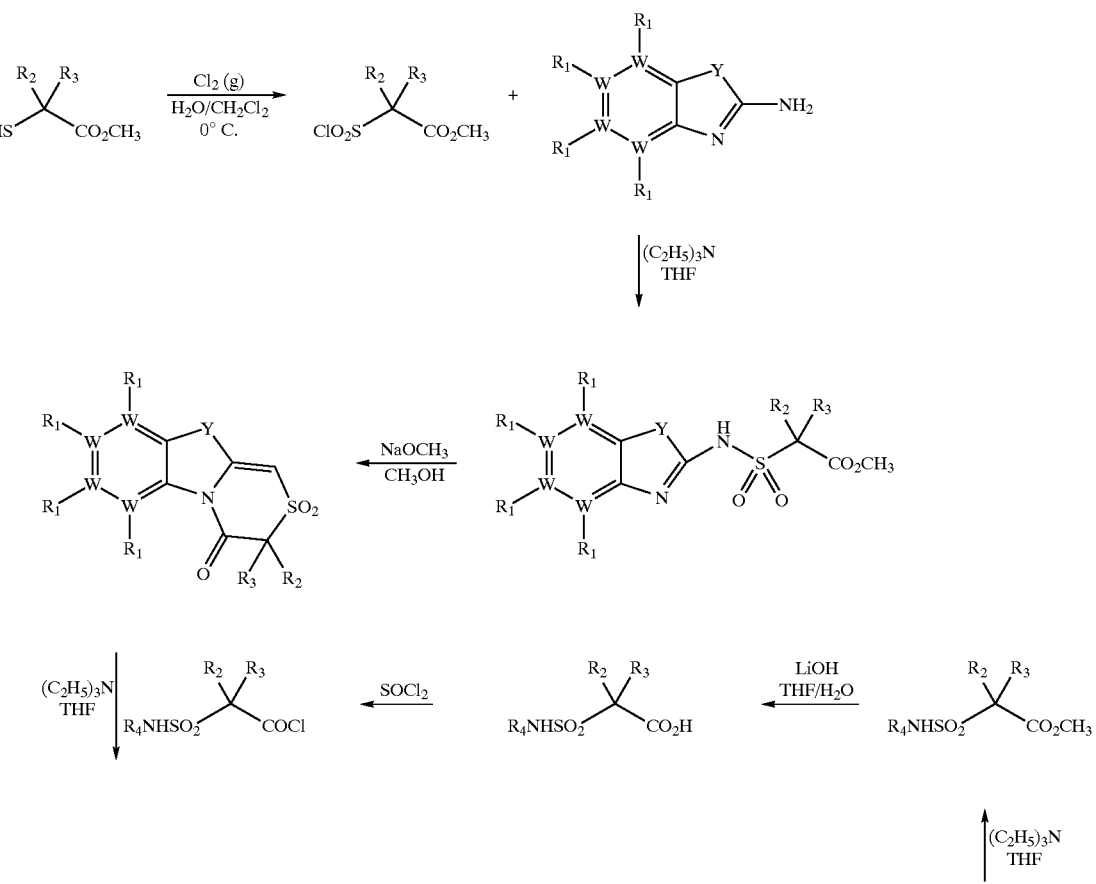

-continued
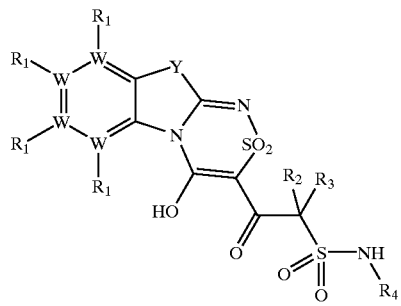
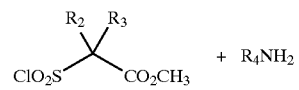
SCHEME IV
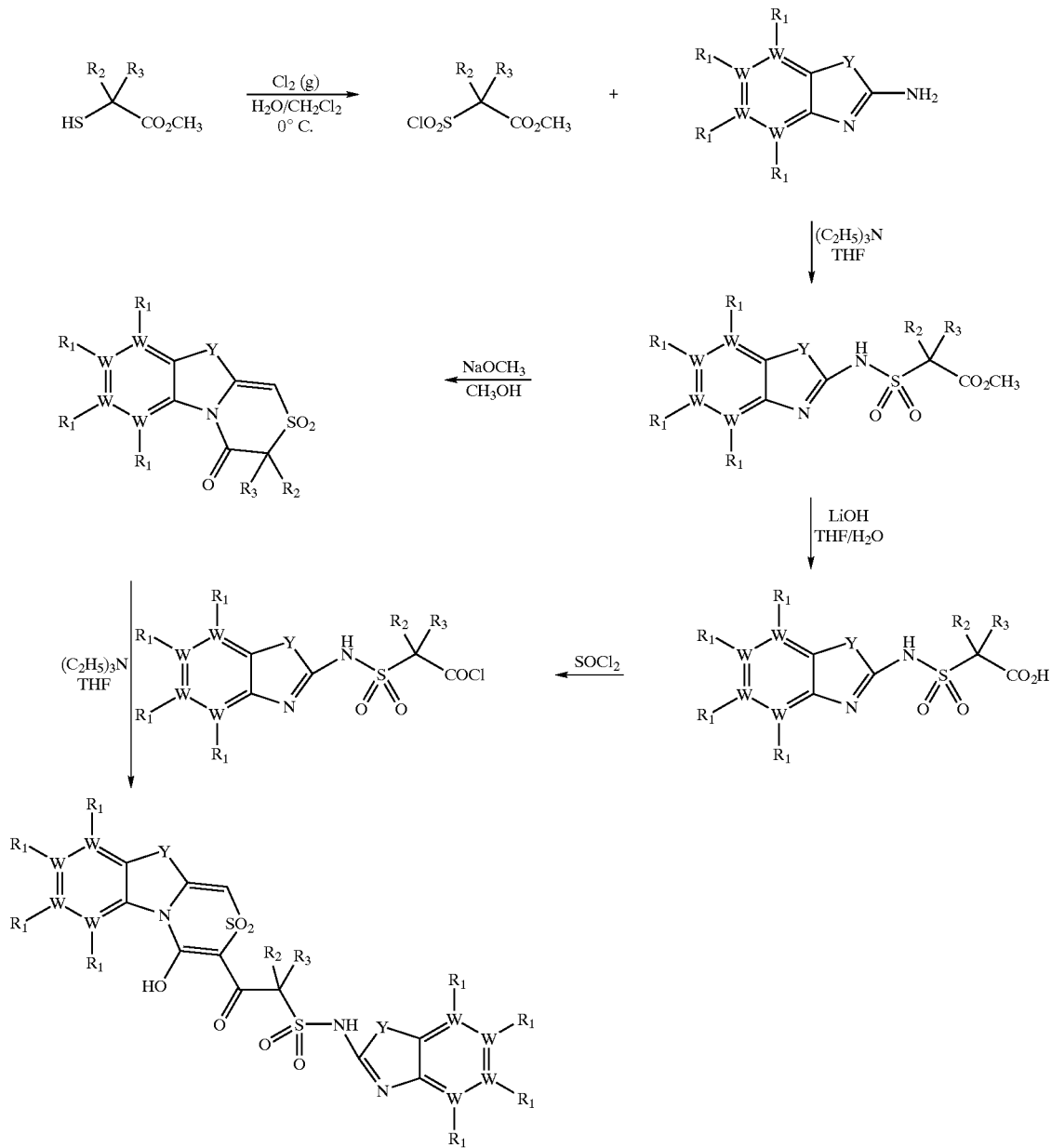
Compounds of formula (I) may then be isolated using typical isolation and purification techniques known in the art, including, for example, chromatographic and recrystallization methods.

In compounds of formula (I) of the invention, carbon atoms to which four non-identical substituents are bonded are asymmetric. For example, when $R_2$ and $R_3$ are not identical, the carbon atom to which $R_2$ and $R_3$ are attached is then bonded to four non-identical groups and as a result the carbon atom is asymmetric. Accordingly, a compound of formula (I) may exist as enantiomers, diastereomers or a mixture thereof. The enantiomers and diastereomers may be separated by chromatographic or crystallization methods, or by other methods known in the art. The asymmetric carbon atom when present in a compound of formula (I) of the invention, may be in one of two configurations (R or S) and both are within the scope of the invention. The presence of small amounts of the opposing enantiomer or diastereomer in the final purified product does not affect the therapeutic or diagnostic application of such compounds.

According to the invention, compounds of formula (I) may be further treated to form pharmaceutically acceptable salts. Treatment of a compound of the invention with an acid or base may form, respectively, a pharmaceutically acceptable acid addition salt and a pharmaceutically acceptable base addition salt, each as defined above. Various inorganic and organic acids and bases known in the art including those defined herein may be used to effect the conversion to the salt.

The invention also relates to pharmaceutically acceptable isomers, hydrates, and solvates of compounds of formula (I). Compounds of formula (I) may also exist in various isomeric and tautomeric forms including pharmaceutically acceptable salts, hydrates and solvates of such isomers and tautomers.

This invention also encompasses prodrug derivatives of the compounds of formula (I). The term "prodrug" refers to a pharmacologically inactive derivative of a parent drug molecule that requires biotransformation, either spontaneous or enzymatic, within the organism to release the active drug. Prodrugs are variations or derivatives of the compounds of formula (I) of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple, etc., depending on the number of biotransformation steps. required to release the active drug within the organism, and indicating the number of functionalities present in a precursor-type form. Prodrug forms often offer advantages of solubility, tissue compatibility, or delayed release in the mammalian organism (Bundgard, *Design of Prodrugs*, pp. 7–9, 21–24, Elsevier, Amsterdam (1985); Silverman, *The Organic Chemistry of Drug Design and Drug Action*, pp. 352–401, Academic Press, San Diego, Calif. (1992)). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

4. Pharmaceutical Compositions and Methods of Treatment

A compound of formula (I) or formula (II) according to the invention may be formulated into pharmaceutical compositions. Accordingly, the invention also relates to a pharmaceutical composition for preventing or treating thrombosis in a mammal, particularly those pathological conditions involving platelet aggregation, containing a therapeutically effective amount of a compound of formula (I) or formula (II) or a pharmaceutically acceptable salt thereof, each as described above, and a pharmaceutically acceptable carrier or agent. Preferably, a pharmaceutical composition of the invention contains a compound of formula (I) or formula (II) or a salt thereof in an amount effective to inhibit platelet aggregation, more preferably, ADP-dependent aggregation, in a mammal, in particular, a human. Pharmaceutically acceptable carriers or agents include those known in the art and are described. below.

Pharmaceutical compositions of the invention may be prepared by mixing the compound of formula (I) or formula (II) with a physiologically acceptable carrier or agent. Pharmaceutical compositions of the invention may further include excipients, stabilizers, diluents and the like and may be provided in sustained release or timed release formulations. Acceptable carriers, agents, excipients, stablilizers, diluents and the like for therapeutic use are well known in the pharmaceutical field, and are described, for example, in *Remington's Pharmaceutical Sciences*, Mack Publishing Co., ed. A. R. Gennaro (1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as TWEEN, or polyethyleneglycol.

Methods for preventing or treating thrombosis in a mammal embraced by the invention administer a therapeutically effective amount of a compound of formula (I) or formula (II) alone or as part of a pharmaceutical composition of the invention as described above to a mammal, in particular, a human. Compounds of formula (I) or formula (II) and pharmaceutical compositions of the invention containing a compound of formula (I) or formula (II) of the invention are suitable for use alone or as part of a multi-component treatment regimen for the prevention or treatment of cardiovascular diseases, particularly those related to thrombosis. For example, a compound or pharmaceutical composition of the invention may be used as a drug or therapeutic agent for any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia; deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and protheses.

Compounds and pharmaceutical compositions of the invention may also be used as part of a multi-component treatment regimen in combination with other therapeutic or diagnostic agents in the prevention or treatment of thrombosis in a mammal. In certain preferred embodiments, compounds or pharmaceutical compositions of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. Coadministration may also allow for application of reduced doses of the thrombolytic agents and therefore minimize potential hemorrhagic side-effects. Compounds and pharmaceutical compositions of the invention may also act in a synergistic fashion to prevent reocclusion following a successful thrombolytic therapy and/or reduce the time to reperfusion.

The compounds and pharmaceutical compositions of the invention may be utilized in vivo, ordinarily in mammals such as primates, (e.g., humans), sheep, horses, cattle, pigs, dogs, cats, rats and mice, or in vitro. The biological properties, as defined above, of a compound or a pharmaceutical composition of the invention can be readily characterized by methods that are well known in the art such as, for example, by in vivo studies to evaluate antithrombotic efficacy, and effects on hemostasis and hematological parameters.

Compounds and pharmaceutical compositions of the invention may be in the form of solutions or suspensions. In the management of thromboticdisorders the compounds or pharmaceutical compositions of the invention may also be in such forms as, for example, tablets, capsules or elixirs for oral administration, suppositories, sterile solutions or suspensions or injectable administration, and the like, or incorporated into shaped articles. Subjects (typically mammalian) in need of treatment using the compounds or pharmaceutical compositions of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound of formula (I) or formula (II) employed, the specific use for which the compound or pharmaceutical composition is employed, and other factors which those skilled in the medical arts will recognize.

Dosage formulations of compounds of formula (I) or formula (II) or pharmaceutical compositions of the invention to be used for therapeutic administration must be sterile. Sterility is readily accomplished by filtration through sterile membranes such as 0.2 micron membranes, or by other conventional methods. Formulations typically will be stored in a solid form, preferably in a lyophilized form. While the preferred route of administration is orally, the dosage formulations of compounds of formula (I) or formula (II) or pharmaceutical compositions of the invention may also be administered by injection, intravenously (bolus and/or infusion), subcutaneously, intramuscularly, colonically, rectally, nasally, transdermally or intraperitoneally. A variety of dosage forms may be employed as well including, but not limited to, suppositories, implanted pellets or small cylinders, aerosols, oral dosage formulations and topical formulations such as ointments, drops and dermal patches. The compounds of formula (I) or formula (II) and pharmaceutical compositions of the invention may also be incorporated into shapes and articles such as implants which may employ inert materials such biodegradable polymers or synthetic silicones as, for example, SILASTIC, silicone rubber or other polymers commercially available. The compounds and pharmaceutical compositions of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

Therapeutically effective dosages may be determined by either in vitro or in vivo methods. For each particular compound or pharmaceutical composition of the invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the bodily fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, i.e., platelet ADP receptor inhibition, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound of formula (I) or formula (II) is compounded with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

Typical adjuvants which may be incorporated into tablets, capsules and the like include, but are not limited to, binders such as acacia, cornstarch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

The following examples are given to illustrate the invention. It should be understood, however, that the invention is not to be limited to the specific conditions or details set forth in these examples.

EXAMPLES

Methods and Materials

Compounds 1–8 of formula (III), respectively, Examples 1–8 were synthesized using standard laboratory glassware and techniques known in the art and are summarized in Table 2 below:

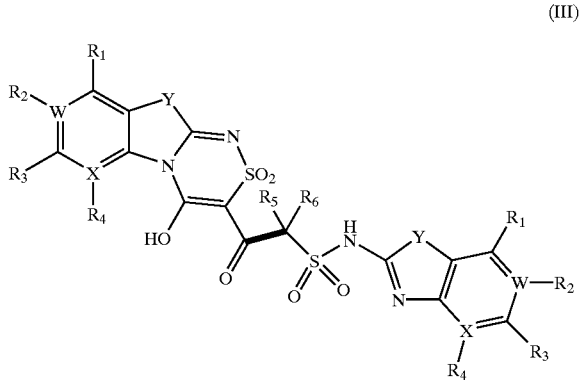

(III)

TABLE 2

Summary of Compounds 1–8 of Formula (III).

| Compound | $R_1$ | $R_2$ | $R_3$ | $R_4$ | $R_5$ | $R_6$ | W | X | Y |
|---|---|---|---|---|---|---|---|---|---|
| 1 | H | OCH$_2$CH$_3$ | H | H | H | H | C | C | S |
| 2 | H | H | H | H | H | H | C | C | S |
| 3 | H | CH$_3$ | H | H | H | H | C | C | S |
| 4 | H | Cl | H | H | H | H | C | C | S |
| 5 | H | SO$_2$CH$_3$ | H | H | H | H | C | C | S |
| 6 | H | NO$_2$ | H | H | H | H | C | C | S |
| 7 | H | F | H | H | H | H | C | C | S |
| 8 | H | OCH$_3$ | H | H | H | H | C | C | S |

The aminobenzothiazoles were purchased from Aldrich (Milwaukee, Wis.) or Lancaster, (Windham, N.H.). Chlorosulfonylacetyl chloride was purchased from Aldrich. Solvents used were of HPLC grade or better. Tetrahydrofuran was distilled from sodium benzophenone ketyl before use.

Exact mass determination for compound 1 was obtained on a VG Analytical ZAB 2-SE High Resolution Fast Atom Bombardment Mass Spectrometer using a cesium ion gun to generate ions. Conventional mass spectral data for compounds 2–9 were obtained using either direct chemical ionization or an electrospray technique. NMR data were obtained on a Varian (Palo Alto, Calif.) Unity+400 MHz instrument utilizing a probe capable of detecting $^1$H, $^{13}$C, $^{19}$F, and $^{31}$P nuclei. Analytical HPLC data were obtained using a C$_{18}$ column running a gradient from 95:5 water:acetonitrile (w/0.1% trifluoroacetic acid) to 20:80 water:acetonitrile (w/0.1% trifluoroacetic acid) over 30 minutes. The instrument used for data collection was a Waters (Bedford, Mass.) Model 600 controller connected to a Waters Model 996 photodiode array detector interfaced with a Waters Model 717 autosampler. Data collection and analysis were computer-controlled using the Millenium software package proprietary to the Waters system. Preparative HPLC data were obtained using a 5.0 cm diameter C$_{18}$ column under the solvent elution conditions indicated in the specific examples. The instrument used for sample preparation was a Waters Model 600 controller connected to a Waters Model 490 four-wavelength detector interfaced with an X-Y stripchart recorder to monitor peak elution as a function of time.

Example 1

Synthesis of N$^1$-(6-Ethoxy-1,3-benzothiazol-2-yl)-2-(8-ethoxy-4-hydroxy-2,2-dioxo-2H-2l$^6$-benzo[4,5][1,3]thiazolo[2,3-c][1,2,4]thiadiazin-3-yl)-2-oxo-1-ethanesulfonamide (Compound 1)

To a solution of 2.58 g (13.1 mmol) of 6-ethoxy-2-aminobenzothiazole dissolved in 50 mL of anhydrous tetrahydrofuran stirring at room temperature under argon was added 3.0 mL (21.5 mmol) of triethylamine. Into a dropping funnel was transferred a solution of 1.0 g (5.65 mmol) of chlorosulfonylacetyl chloride dissolved in 10 mL of anhydrous tetrahydrofuran. Upon dropwise addition of the chlorosulfonylacetyl chloride to the aminoazole solution, a heavy precipitate formed immediately. The resultant mixture was stirred for 2 days.

The reaction was quenched by addition of water. The biphasic solution was acidified with 10% HCl and extracted twice with ethyl acetate. The combined organic extracts were washed twice with saturated brine, dried with magnesium sulfate, and concentrated in vacuo. There was obtained a yellow-brown solid.

The title compound was obtained in pure form from the isolated solid using reverse phase preparative HPLC. HPLC Conditions: flow rate=40 mL per min; isocratic at 100% H$_2$O (containing 0.1% trifluoroacetic acid) for ten minutes, followed by a linear gradient to a final solvent composition of 40% H$_2$O: 60% CH$_3$CN (containing 0.1% trifluoroacetic acid) occurring over 60 minutes. The desired material, Compound 1, (64.1 mg, 0.11 mmol, 1% yield) was obtained as a lyophilized yellow powder from fractions eluting with a solvent composition containing 50%–58% CH$_3$CN.

HRMS for C$_{22}$H$_{20}$N$_4$O$_8$S$_4$: M+H expected: 597.0242; M+H obtained: 597.0248

Analytical HPLC retention time: 24.1 minutes (l$_{max}$=295 nm)

$^1$H NMR (DMSO-d6): 7:95–7.97 (d); 7.33(d); 7.27 (d); 6.93–6.95 (d); 6.81–6.83 (dd); 6.49–6.51 (dd); 4.65 (s); 3.93–4.01 (q×2); 1.27–1.31 (t×2)

$^{13}$C NMR (DMSO-d6): 180.84; 167.82; 159.13; 158.95; 156.04; 155.46; 131.09; 130.43; 126.84; 122.83; 119.52; 114.99; 113.53; 113.38; 107.89; 107.74; 101.41; 64.16; 63.93; 63.11; 15.12; 15.06

$^1$H-$^{13}$C HETCOR 2D NMR (DMSO-d6): correlations between 7.96 and 119.5; 7.33 and 107.9; 7.27 and 107.7; 6.93 and 113.5; 6.82 and 114.9; 6.50 and 113.3; 4.65 and 63.1; 3.96 and 64.1; 1.30 and 15.1

Example 2

Synthesis of N$^1$-(1,3-benzothiazol-2-yl)-2-(4-hydroxy-2,2-dioxo-2H-2l$^6$-benzo[4,5][1,3]thiazolo[2,3-c][1,2,4]thiadiazin-3-yl)-2-oxo-1-ethanesulfonamide (Compound 2)

To a solution of 0.152 g (1.01 mmol) of 2-aminobenzothiazole dissolved in 10 mL of anhydrous tetrahydrofuran stirring at room temperature under argon was added 0.70 mL (5.02 mmol) of triethylamine. Into a dropping funnel was transferred a solution of 0.11 mL (1.03 mmol) of chlorosulfonylacetyl chloride dissolved in 3 mL of anhydrous tetrahydrofuran. Upon dropwise addition of the chlorosulfonylacetyl chloride to the aminoazole solution, a heavy precipitate formed immediately. The resultant mixture was stirred for 18 hours.

The reaction was quenched by addition of water. The biphasic solution was acidified with 10% citric acid and extracted twice with ethyl acetate. The combined organic extracts were washed twice with saturated brine, dried with magnesium sulfate, and concentrated in vacuo. There was obtained a yellow-orange solid.

The title compound was obtained in pure form from the isolated solid using reverse phase preparative HPLC. HPLC Conditions: flow rate=40 mL per min; isocratic at 80% $H_2O$: 20% $CH_3CN$ (containing 0.1% trifluoroacetic acid) for ten minutes, followed by a linear gradient to a final solvent composition of 30% $H_2O$: 70% $CH_3CN$ (containing 0.1% trifluoroacetic acid) occurring over 50 minutes. The desired material, Compound 2, (20.0 mg, 0.040 mmol, 4% yield) was obtained as a lyophilized yellow powder from fractions eluting with a solvent composition containing 55%–58% $CH_3CN$.

MS: M+H=509 (electrospray)

Analytical HPLC retention time: 21.5 minutes $^1$H NMR (DMSO-d6): 8.08–8.10 (d); 7.70–7.72 (d); 7.65–7.67 (d); 7.25–7.29 (t); 7.17–7.20 (t); 7.05–7.07 (d); 6.96 (t); 4.65 (s)

Example 3

Synthesis of $N^1$-(6-Methyl-13-benzothiazol-2-yl)-2-(8-methyl-4-hydroxy-2,2-dioxo-2H-2l$^6$-benzo[4,5][1,3]thiazolo[2,3-c][1,2,4]thiadiazin-3-yl)-2-oxo-1-ethanesulfonamide (Compound 3)

To a solution of 0.164 g (1.00 mmol) of 6-methyl-2-aminobenzothiazole dissolved in 10 mL of anhydrous tetrahydrofuran stirring at room temperature under argon was added 0.70 mL (5.02 mmol) of triethylamine. Into a dropping funnel was transferred a solution of 0.11 mL (1.03.mmol) of chlorosulfonylacetyl chloride dissolved in 3 mL of anhydrous tetrahydrofuran. Upon dropwise addition of the chlorosulfonylacetyl chloride to the aminoazole solution, a heavy precipitate formed immediately. The resultant mixture was stirred for 19 hours.

The reaction was quenched by addition of water. The biphasic solution was acidified with 10% citric acid and extracted twice with ethyl acetate. The combined organic extracts were washed twice with saturated brine, dried with magnesium sulfate, and concentrated in vacuo. There was obtained a yellow-orange solid.

The title compound was obtained in pure form from the isolated solid using reverse phase preparative HPLC. HPLC Conditions: flow rate=40 mL per min; isocratic at 80% $H_2O$: 20% $CH_3CN$ (containing 0.1% trifluoroacetic acid) for ten minutes, followed by a linear gradient to a final solvent composition of 30% $H_2O$: 70% $CH_3CN$ (containing 0.1% trifluoroacetic acid) occurring over 50 minutes. The desired material, Compound 3, (23.6 mg, 0.044 mmol, 4% yield) was obtained as a lyophilized yellow powder from fractions eluting with a solvent composition containing 50%–51% $CH_3CN$.

MS: M+H=537 (electrospray)

Analytical HPLC retention time: 23.7 minutes $^1$H NMR (DMSO-d6): 7.98–8.00 (d); 7.50 (s); 7.46 (s); 7.05–7.07 (d); 6.91–6.93 (d); 6.77–6.79 (d); 4.60(s); 2.31 (s); 2.26(s)

Example 4

Synthesis of $N^1$-(6-Chloro-1,3-benzothiazol-2-yl)-2-(8-chloro-4-hydroxy-2,2-dioxo-2H-2l$^6$-benzo[4,5][1,3]thiazolo[2,3-c][1,2,4]thiadiazin-3-yl)-2-oxo-1-ethanesulfonamide (Compound 4)

To a solution of 0.184 g (1.00 mmol) of 6-chloro-2-aminobenzothiazole dissolved in 10 mL of anhydrous tetrahydrofuran stirring at room temperature under argon was added 0.70 mL (5.02 mmol) of triethylamine. Into a dropping funnel was transferred a solution of 0.11 mL (1.03 mmol) of chlorosulfonylacetyl chloride dissolved in 3 mL of anhydrous tetrahydrofuran. Upon dropwise addition of the chlorosulfonylacetyl chloride to the aminoazole solution, a heavy precipitate formed immediately. The resultant mixture was-stirred for 19 hours.

The reaction was quenched by addition of water. The biphasic solution was acidified with 10% citric acid and extracted twice with ethyl acetate. The combined, organic extracts were washed twice with saturated brine, dried with magnesium sulfate, and concentrated in vacuo. There was obtained a yellow-orange solid.

The title compound was obtained in pure form from the isolated solid using reverse phase preparative HPLC. HPLC Conditions: flow rate=40 ml per min; isocratic at 80% $H_2O$: 20% $CH_3CN$ (containing 0.1% trifluoroacetic acid) for ten minutes, followed by a linear gradient to a final solvent composition of 30% $H_2O$: 70% $CH_3CN$ (containing 0.1% trifluoroacetic acid) occurring over 50 minutes. The desired material, Compound 4, (32.7 mg, 0.056 mmol, 6% yield) was obtained as a lyophilized yellow powder from fractions eluting with a solvent composition containing 54%–56% $CH_3CN$.

MS: M+H=577, 579 (electrospray)

Analytical HPLC retention time: 25.1 minutes $^1$H NMR (DMSO-d6): 8.03–8.06 (d); 7.82–7.85 (d×2); 7.23–7.25 (d); 6.92–6.96 (d×2); 4.66 (s)

Example 5

Synthesis of $N^1$-(6-Methylsulfonyl-1,3-benzothiazol-2-yl)-2-(8-methylsulfonyl-4-hydroxy-2,2-dioxo-2H-2l$^6$-benzo[4,5][1,3]thiazolo[2,3-c][1,2,4]thiadiazin-3-yl)-2-oxo-1-ethanesulfonamide (Compound 5)

To a solution of 0.227 g (1.00 mmol) of 6-methylsulfonyl-2-aminobenzothiazole dissolved in 10 mL of anhydrous tetrahydrofuran stirring at room temperature under argon was added 0.70 mL (5.02 mmol) of triethylamine. Into a dropping funnel was transferred a solution of 0.11 mL (1.03 mmol) of chlorosulfonylacetyl chloride dissolved in 3 mL of anhydrous tetrahydrofuran. Upon dropwise addition of the chlorosulfonylacetyl chloride to the aminoazole solution, a heavy precipitate formed immediately. The resultant mixture was stirred for 19 hours.

The reaction was quenched by addition of water. The biphasic solution was acidified with 10% citric acid and extracted with ethyl acetate. A heavy, yellow-orange precipitate formed which was collected by vacuum filtration. The. filtrate contained only trace amounts of material after phase separation and evaporation of organic solvent.

The title compound was obtained in pure form from the isolated solid using reverse phase preparative HPLC. HPLC Conditions: flow rate=40 ml per min; isocratic at 80% $H_2O$: 20% $CH_3CN$ (containing 0.1% trifluoroacetic acid) for ten minutes, followed by a linear gradient to a final solvent composition of 30% $H_2O$: 70% $CH_3CN$ (containing 0.1% trifluoroacetic acid) occurring over 50 minutes. The desired material, Compound 5, (32.7 mg, 0.049 mmol, 5% yield) was obtained as a lyophilized yellow powder from fractions eluting with a solvent composition containing 32%–34% $CH_3CN$.

Analytical HPLC retention time: 18.8 minutes $^1$H NMR (DMSO-d6): 8.37(s); 8.31(s); 8.19–8.21 (d); 7.69–7.71 (d); 7.35–7.37 (d); 7.02–7.04 (d); 4.69 (s); 3.22 (s); 3.18 (s)

Example 6

Synthesis of $N^1$-(6-Nitro-1,3-benzothiazol-2-yl)-2-(8-nitro-4-hydroxy-2,2-dioxo2H-2l$^6$-benzo[4,5][1,3]thiazolo[2,3-c][1,2,4]thiadiazin-3-yl)-2-oxo-1-ethanesulfonamide (Compound 6)

To a solution of 0.195 g (1.00 mmol) of 6-nitro-2-aminobenzothiazole dissolved in 10 mL of anhydrous tetrahydrofuran stirring at room temperature under argon was added 0.70 mL (5.02 mmol) of triethylamine. Into a dropping funnel was transferred a solution of 0.11 mL (1.03 mmol) of chlorosulfonylacetyl chloride dissolved in 3 mL of anhydrous tetrahydrofuran. Upon dropwise addition of the chlorosulfonylacetyl chloride to the aminoazole solution, a heavy precipitate formed immediately. The resultant mixture was stirred for 20 hours.

The reaction was quenched by addition of water. The biphasic solution was acidified with 10% citric acid and extracted twice with ethyl acetate. The combined organic extracts were washed twice with saturated brine, dried with magnesium sulfate, and concentrated in vacuo. A yellow solid was obtained.

The title compound was obtained in pure form from the isolated solid using reverse phase preparative HPLC. HPLC Conditions: flow rate=40 ml per min; isocratic at 80% $H_2O$: 20% $CH_3CN$ (containing 0.1% trifluoroacetic acid) for ten minutes, followed by a linear gradient to a final solvent composition of 30% $H_2O$: 70% $CH_3CN$ (containing 0.1% trifluoroacetic acid) occurring over 50 minutes. The desired material, Compound 6, (50.3 mg, 0.084 mmol, 8% yield) was obtained as a lyophilized yellow powder from fractions eluting with a solvent composition containing 47%–50% $CH_3CN$.

Analytical HPLC retention time: 22.9 minutes $^1$H NMR (DMSO-d6): 8.74 (d); 8.69 (d); 8.20–8.22 (d); 7.99–8.01 (d); 7.69–7.71 (dd); 6.96–6.98 (d); 4.72 (s)

Example 7

Synthesis of $N^1$-(6-Fluoro-1,3-benzothiazol-2-yl)-2-(8-fluoro-4-hydroxy-2,2-dioxo-2H-2l$^6$-benzo[4,5][1,3]thiazolo[2,3-c][1,2,4]thiadiazin-3-yl)-2-oxo-1-ethanesulfonamide (Compound 7)

To a solution of 0.169 g (1.00 mmol) of 6-fluoro-2-aminobenzothiazole dissolved in 10 mL of anhydrous tetrahydrofuran stirring at room temperature under argon was added 0.70 mL (5.02 mmol) of triethylamine. Into a dropping funnel was transferred a solution of 0.11 mL (1.03 mmol) of chlorosulfonylacetyl chloride dissolved in 3 mL of anhydrous tetrahydrofuran. Upon dropwise addition of the chlorosulfonylacetyl chloride to the aminoazole solution, a heavy precipitate formed immediately. The resultant mixture was stirred for 21 hours.

The reaction was quenched by addition of water. The biphasic solution was acidified with 10% citric acid and extracted twice with ethyl acetate. The combined organic extracts were washed twice with saturated brine, dried with magnesium sulfate, and concentrated in vacuo. An orange-brown film was obtained.

The title compound was obtained in pure form from the isolated solid using reverse phase preparative HPLC. HPLC Conditions: flow rate=40 mL per min; isocratic at 80% $H_2O$: 20% $CH_3CN$ (containing 0.1% trifluoroacetic acid) for ten minutes, followed by a linear gradient to a final solvent composition of 30% $H_2O$: 70% $CH_3CN$ (containing 0.1 % trifluoroacetic acid) occurring over 50 minutes. The desired material, Compound 7, (39.2 mg, 0.072 mmol, 7% yield) was obtained as a lyophilized yellow powder from fractions eluting with a solvent composition containing 46%–49% $CH_3CN$.

MS: M-H=543 (negative ion DCI)

Analytical HPLC retention time: 22.5 minutes $^1$H NMR (DMSO-d6): 8.10–8.12 (dd); 7.63–7.68 (d×2); 7.07–7.11 (t); 6.98–7.00 (d); 6.80–6.82 (dd); 4.65 (s)

Example 8

Synthesis of $N^1$-(6-Methoxy-1,3-benzothiazol-2-yl)-2-(8-methoxy-4-hydroxy-2,2-dioxo-2H-2l$^6$-benzo[4,5][1,3]thiazolo[2,3-c][1,2,4]thiadiazin-3-yl)-2-oxo-1-ethanesulfonamide (Compound 8)

To a solution of 0.180 g (1.00 mmol) of 6-methoxy-2-aminobenzothiazole dissolved in 10 mL of anhydrous tetrahydrofuran stirring at room temperature under argon was added 0.70 mL (5.02 mmol) of triethylamine. Into a dropping funnel was transferred a solution of 0.11 mL (1.03 mmol) of chlorosulfonylacetyl chloride dissolved in 3 mL of anhydrous tetrahydrofuran. Upon dropwise addition of the chlorosulfonylacetyl chloride to the aminoazole solution, a heavy precipitate formed immediately. The resultant mixture was stirred for 28 hours.

The reaction was quenched by addition of water. The biphasic solution was acidified with 10% citric acid and extracted twice with ethyl acetate. The combined organic extracts were washed twice with saturated brine, dried with magnesium sulfate, and concentrated in vacuo. An orange foam was obtained.

The title compound was obtained in pure form from the isolated solid using reverse phase preparative HPLC. HPLC Conditions: flow rate=40 mL per min; isocratic at 80% $H_2O$: 20% $CH_3CN$ (containing 0.1% trifluoroacetic acid) for ten minutes, followed by a linear gradient to a final solvent composition of 30% $H_2O$: 70% $CH_3CN$ (containing 0.1% trifluoroacetic acid) occurring over 50 minutes. The desired material, Compound 8, (9.0 mg, 0.016 mmol, 2% yield) was obtained as a lyophilized yellow powder from fractions eluting with a solvent composition containing 45%–47% $CH_3CN$.

Analytical HPLC retention time: 21.8 minutes $^1$H NMR (DMSO-d6): 7.97–8.01 (dd); 7.36–7.37 (d); 7.31–7.32 (d); 6.95–6.97 (d); 6.83–6.87 (dd); 6.51–6.54 (dd); 4.60 (s); 3.74 (s); 3.71 (s)

Example 9

Pharmacological Assays and Results

The pharmacological activity of Compounds 1–8 as prepared in, respectively, Examples 1–8 was determined by the following in vitro assays:

I. Inhibition of ADP-Mediated Platelet Aggregation in vitro

The effect of test Compounds 1–8 of, respectively, Examples 1–8 on ADP-induced human platelet aggregation was assessed in 96-well microtiter assay. Human venous blood was collected from healthy, drug-free volunteers into ACD (85 mM sodium citrate, 111 mM glucose, 71..4 mM citric acid) containing $PGI_2$ (1.25 ml ACD containing 1.6 $\mu$M $PGI_2$/10 ml blood; $PGI_2$ was from Sigma, St. Louis, Mo.). Platelet-rich plasma (PRP) was prepared by centrifugation at 160×g for 20 minutes at room temperature. Washed platelets were prepared by centrifuging PRP for 10 minutes at 730×g and resuspending the platelet pellet in CGS (13 mM sodium citrate, 30 mM glucose, 120 mM NaCl; 2 ml CGS/10 ml original blood volume) containing 1 U/ml apyrase (grade V, Sigma, St. Louis, Mo.). After incubation at 37° C. for 15 minutes, the platelets were collected by centrifugation at 730×g for 10 minutes and resuspended at a concentration of 3×10$^8$ platelets/ml in Hepes-Tyrode's buffer (10 mM Hepes; 138 mM NaCl, 5.5 mM glucose, 2.9 mM KCl, 12 mM NaHCO$_3$, pH 7.4) containing 0.1% bovine serum albumin, 1 mM CaCl$_2$ and 1 mM MgCl$_2$. This platelet suspension was kept >45 minutes at 37° C. before use in aggregation assays.

Inhibition of ADP-dependent aggregation was determined in 96-well flat-bottom microtiter plates using a microtiter plate shaker and plate reader similar to the procedure described by Frantantoni et al., *Am. J. Clin. Pathol.* 94, 613 (1990). All steps were performed at room temperature. The total reaction volume of 0.2 ml/well included in Hepes-Tyrodes buffer/0.1% BSA: 4.5×10$^7$ apyrase-washed platelets, 0.5 mg/ml human fibrinogen (American Diagnostica, Inc., Greenwich, Conn.), serial dilutions of test compounds (buffer for control wells) in 0.6% DMSO. After about 5 minutes preincubation at room temperature, ADP was added to a final concentration of 2 $\mu$M which induces submaximal aggregation. Buffer was added instead of ADP to one set of control wells (ADP$^-$control). The OD of the samples was then determined at 490 nm using a microtiter plate reader (Softmax, Molecular Devices, Menlo Park, Calif.) resulting in the 0 minute reading. The plates were then agitated for 5 min on a microtiter plate shaker and the 5 minute reading obtained in the plate reader. Aggregation was calculated from the decrease of OD at 490 nm at t=5 minutes compared to t=0 minutes and expressed as % of the decrease in the ADP control samples corrected for changes in the unaggregated control samples.

In some experiments, 0.3 mM 8-sulphophenyltheophylline (8-SPT, Sigma, St. Louis, Mo.) was added to the reaction to block any potential adenosine receptor activity of test compounds.

Results

The data in Table 2 show the mean of 3–12 independent IC$_{50}$ experiments each performed in duplicate. Compounds 1–8 inhibited ADP-dependent aggregation of human platelets with IC$_{50}$s from 180 nM to >120 $\mu$M. Compound 1 was also tested in the presence of 8-sulphophenyltheophylline, an adenosine receptor antagonist. The potency of compound 1 was not reduced indicating that the anti-platelet activity was not mediated by platelet adenosine receptors.

II. Inhibition of [$^3$H]2-MeS-ADP Binding to Platelets

To determine whether the effect of test Compounds 1–8 of, respectively, Examples 1–8 on ADP-dependent platelet aggregation is mediated by interaction with platelet ADP receptors, their potency of inhibition of [$^3$H]2-MeS-ADP binding to whole platelets was determined. 2-MeS-ADP (2-methylthioadenosine 5'-diphosphate) is a potent agonist of ADP responses in platelets and at least the majority of high-affinity [$^3$H]2-MeS-ADP binding sites are considered to reflect functional ADP receptors (Mills, *Thromb. Hemost.* 76, 835 (1996); Savi et al., *Med. Res. Rev.* 16, 159 (1996)). [$^3$H]2-MeS-ADP binding experiments were routinely performed with outdated human platelets collected by standard procedures at hospital blood banks. Apyrase-washed outdated platelets were prepared as follows (all steps at room temperature, if not indicated otherwise):

Outdated platelet suspensions were diluted with 1 volume of CGS and platelets pelleted by centrifugation at 1900×g for 45 minutes. Platelet pellets were resuspended at 3–6×10$^9$ platelets /ml in CGS containing 1 U/ml apyrase (grade V, Sigma, St. Louis, Mo.) and incubated for 15 minutes at 37° C. After centrifugation at 730×g for 20 minutes, pellets were resuspended in Hepes-Tyrode's buffer containing 0.1% BSA (Sigma, St. Louis, Mo.) at a concentration of 6.66×10$^8$ platelets/ml. Binding experiments were performed after >45 minutes resting of the platelets.

Alternatively, binding experiments were performed with fresh human platelets prepared as described in I.(Inhibition of ADP-Mediated Platelet Aggregation in vitro), except that platelets were resuspended in Hepes-Tyrode's buffer containing 0.1% BSA (Sigma, St. Louis, Mo.) at a concentration of 6.66×10$^8$ platelets/ml. Very similar results were obtained with fresh and outdated platelets (see below).

A platelet ADP receptor binding assay using the tritiated potent agonist ligand [$^3$H]2-MeS-ADP, fresh platelets from rats and rapid filtration has been described (Savi et al., *J. Pharmacol. Exp. Ther.* 269, 772 (1994)). A binding assay in a 96-well microtiter format using outdated or fresh human platelets and the radioligand [$^3$H]2-MeS-ADP ([$^3$H]2-methylthioadenosine-5'-diphosphate, ammonium salt; specific activity 49 Ci/mmole, obtained by custom synthesis from Amersham Life Science, Inc., Arlington Heights, Ill.) has been developed. All steps were performed at room temperature unless indicated otherwise.

In an assay volume of 0.2 ml Hepes-Tyrode's buffer with 0.1% BSA and 0.6% DMSO, 1×10$^8$ apyrase-washed platelets were preincubated in 96-well flat bottom microtiter plates for 5 minutes with serial dilutions of test compounds before addition of 1 nM [$^3$H]2-MeS-ADP. Total binding was determined in the absence of test compounds. Samples for nonspecific binding contained 10$^{-5}$ M unlabelled 2-MeS-ADP (RBI, Natick, Mass.). After incubation for 15 minutes at room temperature, unbound radioligand was separated by rapid filtration and two washes with cold (4–8° C.) Binding Wash Buffer (10 mM Hepes pH 7.4, 138 mM NaCl) using a 96-well cell harvester (Minidisc 96, Skatron Instruments, Sterling, Va.) and 8×12 GF/C glassfiber filtermats (Printed Filtermat A, for 1450 Microbeta, Wallac Inc., Gaithersburg, Md.). The platelet-bound radioactivity on the filtermats was determined in a scintillation counter (Microbeta 1450, Wallac Inc., Gaithersburg, Md.). Specific binding was determined by subtraction of non-specific binding from total binding, and specific binding in the presence of test compounds was expressed as % of specific binding in the absence of test compounds dilutions.

Results

The data in Table 2 provide the mean of 2–8 independent IC$_{50}$ experiments each performed in duplicate with outdated platelets. Compounds 1–8 inhibited binding of 1 nM [$^3$H] 2-MeS-ADP to human platelets with IC$_{50}$s from 170 nM to 37 $\mu$M. Compound 1 was also tested with fresh platelets, resulting in an IC$_{50}$ of 160±50 nM (n=3), suggesting that very similar IC$_{50}$s were obtained with outdated and fresh platelets. There was a good correlation between the IC$_{50}$s of these compounds for ADP-dependent platelet aggregation and [$^3$H]2-MeS-ADP binding, suggesting that the anti-platelet activity was specifically mediated by ADP receptors.

TABLE 2

Inhibition of ADP-Dependent Platelet Aggregation and [$^3$H]2-MeS-ADP Binding

| Compound | IC$_{50}$ ($\mu$M) | |
| --- | --- | --- |
|  | Aggregation | Binding |
| 1 | 0.18 | 0.17 |
| 2 | 26 | 21 |
| 3 | 9.5 | 22 |
| 4 | 64 | 35 |
| 5 | 0.7 | 1.8 |
| 6 | 50 | 35 |
| 7 | >120 | 37 |
| 8 | 1.5 | 0.8 |

III. hP2Y$_1$ Receptor Activity Assay

Platlet ADP receptors are considered members of the P2 family of cell surface receptor subtypes that are activated by purine and/or pyrimidine nucleotides (North et al., *Curr. Opin. Neurobiol.* 7, 346 (1997); Harden et al., *Annu. Rev. Pharmacol. Toxicol.* 35, 541 (1995)). Recent studies with cells expressing a cloned member of this family, the human P2Y$_1$ receptor (hP2Y$_1$), suggest that its pharmacological profile might be very similar to platelet ADP receptors mediating aggregation (Gachet et al., *Thromb. Hemost.* 78, 271 (1997)). Therefore, hP2Y$_1$ receptor activity of test compounds was assessed by measuring agonist-induced intracellular calcium mobilization in a mammalian cell line expressing the cloned receptor gene. For this purpose, a genomic fragment encompassing the entire open reading frame of the human P2Y$_1$ receptor plus 220 bp of 3' untranslated region and 10 bp 5' to the ATG initiation codon was isolated from human genomic DNA using standard molecular biology techniques. The deduced amino acid sequence was as described (Schachter et al., *Br. J. Pharmacol.* 118, 167 (1996)). This fragment was cloned into the mammalian expression vector pcINeo (Promega, Madison, Wis.) and transfected into Jurkat cell (American Type Culture Collection, Rockville, Md.) using standard procedures resulting in the clonal cell line hP2Y1-JA7 stably expressing the hP2Y$_1$ receptor.

For intracellular calcium measurements, cells were collected by centrifugation, washed and resuspended in Hepes-Tyrodes buffer/0.1% BSA/1 mM CaCl$_2$ at 10$^7$ cells/ml at 37° C. Fura-2AM (Molecular Probes, Eugene, Oreg.) was added to 4 $\mu$M in the presence of 0.008% Pluronic F-27 (Molecular Probes, Eugene, Oreg.) and incubation continued for 30 minutes at 37° C. in the dark with gentle agitation. Cells were collected by centrifugation and incubated for 15 minutes at 37° C. in buffer with 1 U apyrase/ml. Cells were then centrifuged and resuspended at 4° C. and 2×10$^6$ cells/ml. Starting 30 min. after resuspension intracellular calcium measurements were performed with an spectrofluorimeter (AB2, SLM-Aminco, Spectronic Instruments, Rochester, N.Y.) using the ratio method (excitation wavelengths: 340 and 380 nm; emission wavelength: 510 nm). Aliquots of cells (0.5 ml) were warmed up for 1 minute at 37° C. before starting the ratio measurements under stirring and the addition of reagents. Calcium responses were determined for the agonist 2-MeS-ADP (2-methylthioadenosine diphosphate, trisodium salt, RBI, Natick, Ma.) at the submaximal concentration of 10$^{-7}$M in the absence and presence of various concentrations of test compounds. Maximum ratios were determined after lysis of cells with 100 $\mu$M digitonin, minimum ratios after addition of 20 mM iris and 10 mM EGTA. Fluorescence ratio measurements were converted to calcium concentration traces based on the Grynkiewicz equation and a K$_D$ of 224 nm (Grynkiewicz et al., *J. Bio. Chem.* 260, 3440 (1985)). Increases in intracellular calcium levels were determined by subtraction of baseline levels from peak calcium levels.

Results

Compound 1 was tested in the hP2Y$_1$ receptor assay as a potent representative of this class. The IC$_{50}$ of this compound on 2-MeS-ADP-mediated intracellular calcium mobilization was >100 $\mu$M, suggesting about 1000-fold selectivity for platelet ADP receptors mediating aggregation over a pharmacologically closely related receptor. This relative selectivity over other P2 receptors is a desired property of platelet ADP receptor inhibitors, since it might reduce the occurrence of intolerable side effects, when used therapeutically. By contrast, several known platelet ADP receptor inhibitors, e.g., ATP and derivatives, are nonselective and may be agonists orantagonists of other P2 receptors, possibly resulting in unwanted effects.

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The claimed invention is:

1. A compound of formula (I):

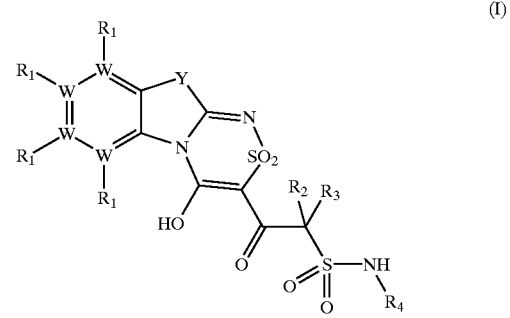

wherein:

W is carbon or nitrogen, wherein at least one W is a carbon;

Y is nitrogen, oxygen, or sulfur;

R$_1$ is, independently, H, C$_1$–C$_6$ alkyl, C$_3$–C$_8$ cycloalkyl, phenyl, pyridyl, pyrimidinyl, hydroxyl, C$_1$–C$_6$ alkoxy, phenoxy, amino, mono-C$_1$–C$_6$ alkylamino, di-C$_1$–C$_6$ alkylamino, monoarylamino, diarylamino, nitro, fluoro, chloro, bromo, iodo, C$_1$–C$_6$ alkylsulfonyl, hydroxycarbonyl, C$_1$–C$_6$ alkoxycarbonyl, absent if W is a nitrogen, or adjacent R$_1$ groups together can form a five- or six-membered alicyclic ring, a six-membered aromatic ring, or a six-membered heteroaromatic ring having from one to two nitrogens, with the proviso that when a sequence of three W—R$_1$ groups form a =N—C(R$_1$)=N— sequence, the R$_1$ bound to carbon is other than a halogen;

R$_2$ and R$_3$ are, independently, H, C$_1$–C$_6$ alkyl, C$_3$–C$_8$ cycloalkyl, or R$_2$ and R$_3$ together form an alicyclic ring containing 3 to 8 carbon atoms; and $R_4$ is a 5- or 6-membered monocyclic or a 5,6-fused bicyclic heterocyclic group having from one to five heteroatom ring members selected from the group consisting of N, O and S, optionally substituted with from 1 to 8 members independently selected from the group consisting of $C_1$–$C_6$ alkyl, $C_3$–$C_8$ cycloalkyl, phenyl, pyridyl, pyrimidinyl, hydroxyl, $C_1$–$C_6$ alkoxy, phenoxy, amino, mono-$C_1$–$C_6$ alkylamino, di-$C_1$–$C_6$ alkylamino, monoarylamino, diarylamino, nitro, fluoro, chloro, bromo, iodo, $C_1$–$C_6$ alkylsulfonyl, hydroxycarbonyl and $C_1$–$C_6$ alkoxycarbonyl.

2. A compound of claim 1, wherein
Y is oxygen or sulfur;
$R_1$ is independently, H, $C_1$–$C_6$ alkyl, phenyl, pyridyl, pyrimidinyl, $C_1$–$C_6$ alkoxy, phenoxy, amino, mono-$C_1$–$C_6$ alkylamino, di-$C_1$–$C_6$ alkylamino, $C_1$–$C_6$ alkylsulfonyl, absent if W is a nitrogen, or adjacent $R_1$ groups together form a six-membered aromatic ring, or a six-membered heteroaromatic ring having from one to two nitrogens; and
$R_2$ and $R_3$ are, independently, H or $C_1$–$C_6$ alkyl.

3. A compound of claim 2, wherein
W is carbon;
Y is sulfur;
$R_1$ is independently, H, pyridyl, pyrimidinyl, amino, mono-$C_1$–$C_6$ alkylamino or di-$C_1$–$C_6$ alkylamino, with the proviso that $R_1$ at the 8 position is $C_1$–$C_6$ alkyl, pyridyl, pyrimidinyl, $C_1$–$C_6$ alkoxy, amino, mono-$C_1$–$C_6$ alkylamino, di-$C_1$–$C_6$ alkylamino or $C_1$–$C_6$ alkylsulfonyl; and
$R_2$ and $R_3$ are each a hydrogen.

4. A compound of formula (II):

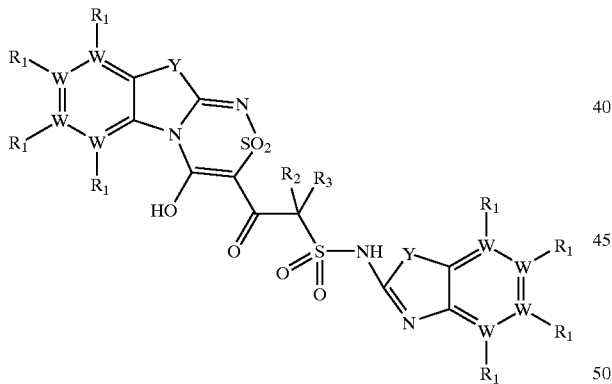

(II)

wherein:
W is carbon or nitrogen, wherein at least one W is a carbon;
Y is nitrogen, oxygen, or sulfur;
$R_1$ is, independently, H, $C_1$–$C_6$ alkyl, $C_3$–$C_8$ cycloalkyl, phenyl, pyridyl, pyrimidinyl, hydroxyl, $C_1$–$C_6$ alkoxy, phenoxy, amino, mono-$C_1$–$C_6$ alkylamino, di-$C_1$–$C_6$ alkylamino, monoarylamino, diarylamino, nitro, fluoro, chloro, bromo, iodo, $C_1$–$C_6$ alkylsulfonyl, hydroxycarbonyl, $C_1$–$C_6$ alkoxycarbonyl, absent if W is a nitrogen, or adjacent $R_1$ groups together may, form a five- or six-membered alicyclic ring, a six-membered aromatic ring, or a six-membered heteroaromatic ring having from one to two nitrogens, with the proviso that when a sequence of three W—$R_1$ groups form a =N—C($R_1$)=N— sequence, the $R_1$ bound to carbon is other than a halogen; and
$R_2$ and $R_3$ are, independently, H, $C_1$–$C_6$ alkyl, $C_3$–$C_8$ cycloalkyl, or $R_2$ and $R_3$ together form an alicyclic ring having from 3 to 8 carbon atoms.

5. A compound of claim 4, wherein said compound is selected from the group consisting of:
(i) $N^1$-(6-Ethoxy-1,3-benzothiazol-2-yl)-2-(8-ethoxy-4-hydroxy-2,2-dioxo-2H-2l$^6$-benzo[4,5][1,3]thiazolo[2,3-c][1,2,4]thiadiazin-3-yl)-2-oxo-1-ethanesulfonamide,
(ii) $N^1$-(1,3-benzothiazol-2-yl)-2-(4-hydroxy-2,2-dioxo-2H-2l$^6$-benzo[4,5][1,3]thiazolo[2,3-c][1,2,4]thiadiazin-3-yl)-2-oxo-1-ethanesulfonamide,
(iii) $N^1$-(6-Methyl-1,3-benzothiazol-2-yl)2-(8-methyl-4-hydroxy-2,2-dioxo-2H-2l$^6$-benzo[4,5][1,3]thiazolo[2,3-c][1,2,4]thiadiazin-3-yl)-2-oxo-1-ethanesulfonamide,
(iv) $N^1$-(6-Chloro-1,3-benzothiazol-2-yl)-2-(8-chloro-4-hydroxy-2,2-dioxo-2H-2l$^6$-benzo[4,5][1,3]thiazolo[2,3-c][1,2,4]thiadiazin-3-yl)-2-oxo-1-ethanesulfonamide,
(v) $N^1$-(6-Methylsulfonyl-1,3-benzothiazol-2-yl)-2-(8-methylsulfonyl-4-hydroxy-2,2-dioxo-2H-2l$^6$-benzo[4,5][1,3]thiazolo[2,3-c][1,2,4]thiadiazin-3-yl)-2-oxo-1-ethanesulfonamide,
(vi) $N^1$-(6-Nitro-1,3-benzothiazol-2-yl)-2-(8-nitro-4-hydroxy-2,2-dioxo-2H-2l$^6$-benzo[4,5][1,3]thiazolo[2,3-c][1,2,4]thiadiazin-3-yl)-2-oxo-1-ethanesulfonamide,
(vii) $N^1$-(6-Fluoro-1,3-benzothiazol-2-yl)-2-(8-fluoro-4-hydroxy-2,2-dioxo-2H-2l$^6$-benzo[4,5][1,3]thiazolo[2,3-c][1,2,4]thiadiazin-3-yl)-2-oxo-1-ethanesulfonamide, and
(viii) $N^1$-(6-Methoxy-1,3-benzothiazol-2-yl)-2-(8-methoxy-4-hydroxy-2,2-dioxo-2H-2l$^6$-benzo[4,5][1,3]thiazolo[2,3-c][1,2,4]thiadiazin-3-yl)-2-oxo-1-ethanesulfonamide.

6. A compound of claim 1, wherein W is carbon.
7. A compound of claim 6, wherein:
Y is sulfur;
$R_2$ and $R_3$ are each H; and
$R_4$ is:

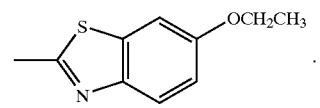

8. A pharmaceutical composition comprising a compound of formula (I):

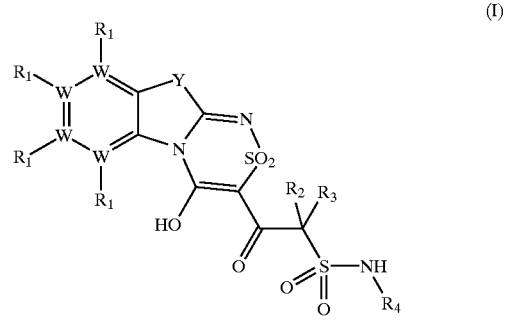

(I)

wherein:
W is carbon or nitrogen, wherein at least one W is a carbon;
Y is nitrogen, oxygen, or sulfur;
$R_1$ is, independently, H, $C_1$–$C_6$ alkyl, $C_3$–$C_8$ cycloalkyl, phenyl, pyridyl, pyrimidinyl, hydroxyl, $C_1$–$C_6$ alkoxy, phenoxy, amino, mono-$C_1$–$C_6$ alkylamino, di-$C_1$–$C_6$ alkylamino, monoarylamino, diarylamino, nitro, fluoro, chloro, bromo, iodo, $C_1$–$C_6$ alkylsulfonyl, hydroxycarbonyl, $C_1$–$C_6$ alkoxycarbonyl, absent if W is a nitrogen, or adjacent $R_1$ groups together can form a five- or six-membered alicyclic ring, a six-membered aromatic ring, or a six-membered heteroaromatic ring having from one to two nitrogens, with the proviso that when a sequence of three W—$R_1$ groups form a =N—C($R_1$)N— sequence, the $R_1$ bound to carbon is other than a halogen;

$R_2$ and $R_3$ are, independently, H, $C_1$–$C_6$ alkyl, $C_3$–$C_8$ cycloalkyl, or $R_2$ and $R_3$ together form an alicyclic ring containing 3 to 8 carbon atoms;

$R_4$ is a 5- or 6-membered monocyclic or a 5,6-fused bicyclic heterocyclic group having from one to five heteroatom ring members selected from the group consisting of N, O and S, optionally substituted with from 1 to 8 members independently selected from the group consisting of $C_1$–$C_6$ alkyl, $C_3$–$C_8$ cycloalkyl, phenyl, pyridyl, pyrimidinyl, hydroxyl, $C_1$–$C_6$ alkoxy, phenoxy, amino, mono-$C_1$–$C_6$ alkylamino, di-$C_1$–$C_6$ alkylamino, monoarylamino, diarylamino, nitro, fluoro, chloro, bromo, iodo, $C_1$–$C_6$ alkylsulfonyl, hydroxycarbonyl and $C_1$–$C_6$ alkoxycarbonyl; or a pharmaceutically acceptable salt thereof; and a pharmaceutically acceptable excipient.

9. The pharmaceutical composition of claim 8, wherein Y is oxygen or sulfur;

$R_1$ is independently, H, $C_1$–$C_6$ alkyl, phenyl, pyridyl, pyrimidinyl, $C_1$–$C_6$ alkoxy, phenoxy, amino, mono-$C_1$–$C_6$ alkylamino, di-$C_1$–$C_6$ alkylamino, $C_1$–$C_6$ alkylsulfonyl, absent if W is a nitrogen, or adjacent $R_1$ groups together form a six-membered aromatic ring, or a six-membered heteroaromatic ring having from one to two nitrogens; and $R_2$ and $R_3$ are, independently, H or $C_1$–$C_6$ alkyl.

10. The pharmaceutical composition of claim 9, wherein W is carbon;

Y is sulfur;

$R_1$ is independently, H, pyridyl, pyrimidinyl, amino, mono-$C_1$–$C_6$ alkylamino or di-$C_1$–$C_6$ alkylamino, with the proviso that $R_1$ at the 8 position is $C_1$–$C_6$ alkyl, pyridyl, pyrimidinyl, $C_1$–$C_6$ alkoxy, amino, mono-$C_1$–$C_6$ alkylamino, di-$C_1$–$C_6$ alkylamino or $C_1$–$C_6$ alkylsulfonyl; and $R_2$ and $R_3$ are each a hydrogen.

11. A pharmaceutical composition comprising: a compound of formula (II):

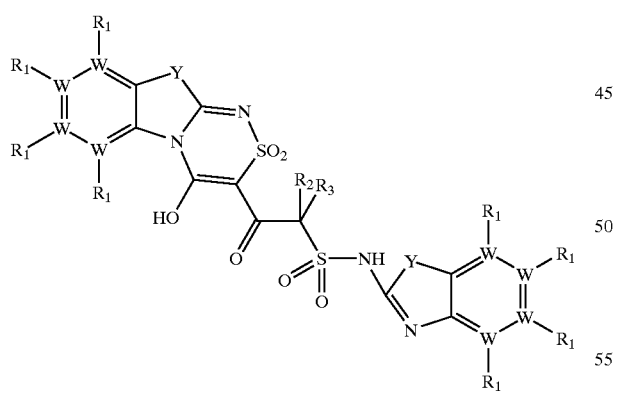

(II)

wherein:
W is carbon or nitrogen, wherein at least one W is a carbon;

Y is nitrogen, oxygen, or sulfur;

$R_1$ is, independently, H, $C_1$–$C_6$ alkyl, $C_3$–$C_8$ cycloalkyl, phenyl, pyridyl, pyrimidinyl, hydroxyl, $C_1$–$C_6$ alkoxy, phenoxy, amino, mono-$C_1$–$C_6$ alkylamino, di-$C_1$–$C_6$ alkylamino, monoarylamino, diarylamino, nitro, fluoro, chloro, bromo, iodo, $C_1$–$C_6$ alkylsulfonyl, hydroxycarbonyl, $C_1$–$C_6$ alkoxycarbonyl, absent if W is a nitrogen, or adjacent $R_1$ groups together may form a five- or six-membered alicyclic ring, a six-membered aromatic ring, or a six-membered heteroaromatic ring having from one to two nitrogens, with the proviso that when a sequence of three W—$R_1$ groups form a =N—C($R_1$)=N— sequence, the $R_1$ bound to carbon is other than a halogen;

$R_2$ and $R_3$ are, independently, H, $C_1$–$C_6$ alkyl, $C_3$–$C_8$ cycloalkyl, or $R_2$ and $R_3$ together form an alicyclic ring having from 3 to 8 carbon atoms;

or a pharmaceutically acceptable salt thereof; and a pharmaceutically acceptable excipient.

12. A method for treating thrombosis, said method comprising: administering a therapeutically effective amount of a compound of formula (I):

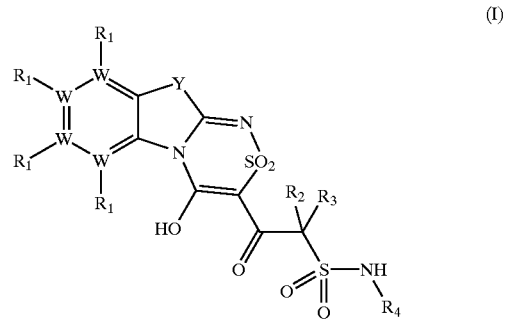

(I)

wherein:
W is carbon or nitrogen, wherein at least one W is a carbon;

Y is nitrogen, oxygen, or sulfur;

$R_1$ is, independently, H, $C_1C_6$ alkyl, $C_3$–$C_8$ cycloalkyl, phenyl, pyridyl, pyrimidinyl, hydroxyl, $C_1$–$C_6$ alkoxy, phenoxy, amino, mono-$C_1$–$C_6$ alkylamino, di-$C_1$–$C_6$ alkylamino, monoarylamino, diarylamino, nitro, fluoro, chloro, bromo, iodo, $C_1$–$C_6$ alkylsulfonyl, hydroxycarbonyl, $C_1$–$C_6$ alkoxycarbonyl, absent if W is a nitrogen, or adjacent $R_1$ groups together can form a five- or six-membered alicyclic ring, a six-membered aromatic ring, or a six-membered heteroaromatic ring having from one to two nitrogens, with the proviso that when a sequence of three W—$R_1$ groups form a =N—C($R_1$)=N— sequence, the $R_1$ bound to carbon is other than a halogen;

$R_2$ and $R_3$ are, independently, H, $C_1$–$C_6$ alkyl, $C_3$–$C_8$ cycloalkyl, or $R_2$ and $R_3$ together form an alicyclic ring containing 3 to 8 carbon atoms;

$R_4$ is a 5- or 6-membered monocyclic or a 5,6-fused bicyclic heterocyclic group having from one to five heteroatom ring members selected from the group consisting of N, O and S, optionally substituted with from 1 to 8 members independently selected from the group consisting of $C_1$–$C_6$ alkyl, $C_3$–$C_8$ cycloalkyl, phenyl, pyndyl, pyrimidinyl, hydroxyl, $C_1$–$C_6$ alkoxy, phenoxy, ammo, mono-$C_1$–$C_6$ alkylamino, di-$C_1$–$C_6$ alkylamino, monoarylamino, diarylamino, nitro, fluoro, chloro, bromo, iodo, $C_1$–$C_6$ alkylsulfonyl, hydroxycarbonyl and $C_1$–$C_6$ alkoxycarbonyl;

or a pharmaceutically acceptable salt thereof.

13. The method of claim 12, wherein
Y is oxygen or sulfur;
$R_1$ is independently, H, $C_1$–$C_6$ alkyl, phenyl, pyridyl, pyrimidinyl, $C_1$–$C_6$ alkoxy, phenoxy, amino, mono-$C_1$–$C_6$ alkylamino, di-$C_1$–$C_6$ alkylamino, $C_1$–$C_6$ alkylsulfonyl, absent if W is a nitrogen, or adjacent $R_1$ groups together form a six-membered aromatic ring, or a six-membered heteroaromatic ring having from one to two nitrogens; and
$R_2$ and $R_3$ are, independently, H or $C_1$–$C_6$ alkyl.
14. The method of claim 12, wherein
W is carbon;
Y is sulfur;

$R_1$ is independently, H, pyridyl, pyrimidinyl, amino, mono-$C_1$–$C_6$ alkylamino or di-$C_1$–$C_6$ alkylamino, with the proviso that $R_1$ at the 8 position is $C_1$–$C_6$ alkyl, pyridyl, pyrimidinyl, $C_1$–$C_6$ alkoxy, amino, mono-$C_1$–$C_6$ alkylamino, di-$C_1C_6$ alkylamino or $C_1$–$C_6$ alkylsulfonyl; and $R_2$ and $R_3$ are each a hydrogen.

15. A method for treating thrombosis, said method comprising: administering a therapeutically effective amount of a compound of formula (II):

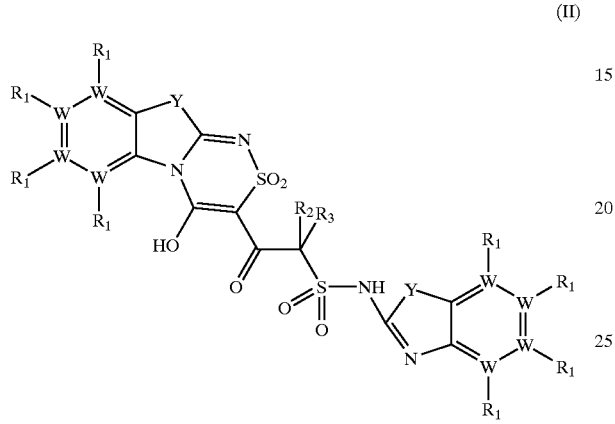

(II)

wherein

W is carbon or nitrogen, wherein at least one W is a carbon;

Y is nitrogen a oxygen, or sulfur;

$R_1$ is, independently, H, $C_1$–$C_6$ alkyl, $C_3$–$C_8$ cycloalkyl, phenyl, pyridyl, pyrimidinyl, hydroxyl, $C_1$–$C_6$ alkoxy, phenoxy, amino, mono-$C_1$–$C_6$ alkylamino, di-$C_1$–$C_6$ alkylamino, monoarylamino, diarylamino, nitro, fluoro, chloro, bromo, iodo, $C_1$–$C_6$ alkylsulfonyl, hydroxycarbonyl, $C_1$–$C_6$ alkoxycarbonyl, absent if W is a nitrogen, or adjacent $R_1$ groups together may form a five- or six-membered alicyclic ring, a six-membered aromatic ring, or a six-membered heteroaromatic ring having from one to two nitrogens, with the proviso that when a sequence of tree W—$R_1$ groups form a =N—C($R_1$)=N— sequence, the $R_1$ bound to carbon is other than a halogen;

$R_2$ and $R_3$ are, independently, H, $C_1$–$C_6$ alkyl, $C_3$–$C_8$ cycloalkyl, or $R_2$ and $R_3$ together form an alicyclic ring having from 3 to 8 carbon atoms;

or a pharmaceutically acceptable salt thereof.

* * * * *

UNITED STATES PATENT AND TRADEMARK OFFICE
CERTIFICATE OF CORRECTION

PATENT NO. : 6,667,306 B1
DATED : December 23, 2003
INVENTOR(S) : Laibelman et al.

It is certified that error appears in the above-identified patent and that said Letters Patent is hereby corrected as shown below:

Title page,
Item [73], replace "Millenium Pharmaceuticals, Inc., Cambridge, MA (US)" with
-- Portola Pharmaceuticals, Inc., South San Francisco, CA (US) --

Column 30,
Line 31, replace "$C_1C_6$" with -- $C_1$-$C_6$ --.
Line 51, replace "pyndyl" with -- pyridyl --.
Line 52, replace "ammo" with -- amino --.

Column 32,
Line 7, after "nitrogen" insert -- , -- and delete "a" --.

Signed and Sealed this

Eleventh Day of May, 2004

JON W. DUDAS
*Acting Director of the United States Patent and Trademark Office*